(12) United States Patent
Hashimoto et al.

(10) Patent No.: US 9,480,446 B2
(45) Date of Patent: Nov. 1, 2016

(54) X-RAY DETECTION SUBMODULE, X-RAY DETECTION MODULE, AND X-RAY CT APPARATUS

(71) Applicant: TOSHIBA MEDICAL SYSTEMS CORPORATION, Otawara-Shi (JP)

(72) Inventors: Atsushi Hashimoto, Otawara (JP); Akira Nishijima, Nasushiobara (JP); Shuya Nambu, Nasushiobara (JP); Yoji Kudo, Otawara (JP); Masahiko Yamazaki, Utsunomiya (JP); Tomonori Asada, Nasushiobara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 171 days.

(21) Appl. No.: 14/261,976

(22) Filed: Apr. 25, 2014

(65) Prior Publication Data

US 2014/0233690 A1    Aug. 21, 2014

Related U.S. Application Data

(63) Continuation of application No. PCT/JP2013/073002, filed on Aug. 28, 2013.

(30) Foreign Application Priority Data

Aug. 29, 2012 (JP) ................. 2012-189162
Aug. 27, 2013 (JP) ................. 2013-175906

(51) Int. Cl.
*H01L 27/146*    (2006.01)
*G01T 1/24*    (2006.01)
*A61B 6/00*    (2006.01)
*G01T 1/20*    (2006.01)
*G01T 5/08*    (2006.01)

(52) U.S. Cl.
CPC ........... *A61B 6/4411* (2013.01); *A61B 6/4233* (2013.01); *A61B 6/4266* (2013.01); *G01T 1/243* (2013.01); *H01L 27/14601* (2013.01); *H01L 27/14634* (2013.01); *H01L 27/14636* (2013.01); *G01T 1/2018* (2013.01); *G01T 5/08* (2013.01)

(58) Field of Classification Search
CPC ........ A61B 6/00; A61B 6/42; A61B 6/4208; A61B 6/4233; A61B 6/4266; A61B 6/44; A61B 6/4411; H01L 21/00; H01L 21/02104; H01L 21/02697; H01L 21/70; H01L 21/71; H01L 21/74; H01L 21/743; H01L 21/77; H01L 23/00; H01L 23/48; H01L 23/481; H01L 23/552; H01L 25/00; H01L 25/03; H01L 25/04; H01L 25/065; H01L 25/0652; H01L 25/0657; H01L 25/16; H01L 25/167; H01L 27/00; H01L 27/04; H01L 27/10; H01L 27/14; H01L 27/142; H01L 27/144; H01L 27/1446; H01L 27/146; H01L 27/14601; H01L 27/14603; H01L 27/14625; H01L 27/14634; H01L 27/14636; H01L 27/14643; H01L 27/14658; H01L 27/14663; H01L 27/14665; H01L 27/14676; H01L 31/00; H01L 31/02; H01L 31/0232; H01L 31/02322; H01L 31/02327; H01L 31/08; H01L 31/085; H01L 33/48; H01L 33/50; H01L 33/501; H01L 33/502; H01L 33/507; H01L 51/00; H01L 51/42; H01L 51/44; H01L 2223/00; H01L 2227/00; H01L 2933/00; H01L 2933/0008; H01L 2933/0033; H01L 2933/0041; G01T 1/00; G01T 1/16; G01T 1/1612; G01T 1/1614; G01T 1/20; G01T 1/2006; G01T 1/2018; G01T 1/24; G01T 1/243; H01P 5/00
See application file for complete search history.

(56) References Cited

U.S. PATENT DOCUMENTS

| | | | |
|---|---|---|---|
| 5,831,269 A * | 11/1998 | Nakamura | G01T 1/2018 250/367 |
| 6,005,911 A * | 12/1999 | Cheung | A61B 6/4233 378/37 |
| 2002/0153492 A1* | 10/2002 | Sekine | G01T 1/2018 250/370.11 |
| 2007/0003006 A1* | 1/2007 | Tkaczyk | G01T 1/2985 378/19 |
| 2012/0223239 A1* | 9/2012 | Bernhardt | G01T 1/2018 250/366 |
| 2013/0112882 A1* | 5/2013 | Osawa | G01T 1/202 250/361 R |

FOREIGN PATENT DOCUMENTS

| | | |
|---|---|---|
| JP | 07-297442 A | 11/1995 |
| JP | 2006-075489 A | 3/2006 |
| JP | 2009-189384 A | 8/2009 |
| JP | 2011-141230 A | 7/2011 |
| JP | 2012-081264 A | 4/2012 |
| JP | 2012-118073 A | 6/2012 |
| WO | WO 03/096070 A1 | 11/2003 |

OTHER PUBLICATIONS

International Search Report issued on Sep. 24, 2013 for PCT/JP2013/073002 filed on Aug. 28, 2013 with English translation.
International Preliminary Report on Patentability and Written Opinion issued Mar. 3, 2015 in PCT/JP2013/073002 (submitting English translation only).

* cited by examiner

*Primary Examiner* — Anastasia Midkiff
(74) *Attorney, Agent, or Firm* — Oblon, McClelland, Maier & Neustadt, L.L.P.

(57) ABSTRACT

An X-ray detection submodule, comprising: a substrate; a photodiode mounted on the substrate; an X-ray detection element configured to detect an X-ray and convert the X-ray into light; and a light waveguide provided between the photodiode and the X-ray detection element, wherein the light waveguide connects the X-ray detection element with the photodiode such that the substrate is inclinedly disposed with respect to an X-ray detection surface of the X-ray detection element.

8 Claims, 6 Drawing Sheets

X-RAY DETECTION SUBMODULE, X-RAY DETECTION MODULE, AND X-RAY CT APPARATUS

CROSS-REFERENCE TO RELATED APPLICATION

This application is a Continuation application of No. PCT/JP2013/73002, filed on Aug. 28, 2013, and the PCT application is based upon and claims the benefit of priority from Japanese Patent Application No. 2012-189162, filed on Aug. 29, 2012, and Japanese Patent Application No. 2013-175906, filed on Aug. 27, 2013, the entire contents all of which are incorporated herein by reference.

FIELD

Embodiments of the present invention relate to an X-ray detection submodule, an X-ray detection module, and an X-ray CT apparatus.

BACKGROUND

An X-ray CT apparatus includes an X-ray source and an X-ray detector, which are opposedly disposed with an object interposed therebetween. The X-ray detector includes a plurality of channels (M channels) of detection elements along a direction perpendicular to a longitudinal direction of a top board (a channel direction), which is a body-axis direction.

Although various types of X-ray detectors are available, it is general in an X-ray CT apparatus to use a scintillation detector which is downsizable. Each detection element of the scintillation detector includes a scintillator and an optical sensor such as a photodiode (PD). The scintillator absorbs an X-ray collimated in a previous stage, causing a generation of fluorescence by the absorption. The PD converts the fluorescence into an electric signal by an optical sensor, and outputs it to a data acquisition system (DAS).

That is, according to the X-ray CT apparatus, an X-ray beam is radiated in a fan shape to a section of the object (hereafter, referred to as a slice surface) from the X-ray source, and the X-ray beam that has transmitted a slice surface of the object is converted into an electric signal for each detection element of the X-ray detector, thereby collecting transmission data.

Moreover, examples of the X-ray CT apparatus include a single-slice X-ray CT apparatus and a multi-slice X-ray CT apparatus. The above described X-ray CT apparatus, which includes M channels of X-ray detectors along the channel direction, and one row of them in the body-axis direction, is called a single slice X-ray CT apparatus.

In contrast, a multi-slice X-ray CT apparatus is configured, compared with the single-slice X-ray CT apparatus, such that the X-ray detector includes, in addition to M channels of detection elements, a plurality of rows (N rows) of detection elements along the direction of body axis of the object. That is, the X-ray detector of the multi-slice X-ray CT apparatus is configured to be a two-dimensional detector for X-ray CT having M channels by N rows of detection elements as a whole.

By the way, in a conventional multi-slice X-ray CT apparatus, X-ray detectors each having M channels by N rows of detection elements are arranged in the channel direction and in the body-axis direction to form an X-ray detection unit for detecting an X-ray by X-ray detectors and DASs. Moreover, the X-ray detector and the DAS are separately constructed and connected by a flexible cable.

In such X-ray detection unit, due to a recent trend of increasing the number of rows of the X-ray CT apparatus, the number of detection elements per a system has remarkably increased. Therefore, to process increased output signals of the X-ray detection unit, it is necessary to efficiently dispose ADC chips included in the DAS for processing the output signals. Moreover, if a shift of trend toward higher resolution occurs in the future, the X-ray detection unit is expected to have an even larger number of detection elements.

Meanwhile, in a conventional connection method, since there is an upper limit in the mounting area and volume in a substrate for mounting detection elements, when mounting an ADC substrate equipped with ADC chips, there is a restriction in the number of them that can be mounted. Moreover, even if an ADC substrate can be mounted, a problem exists in that the distance of the signal wiring from the detection element to the ADC substrate becomes too large so that the signal becomes subject to external noise and also the certainty of the signal deteriorates.

DETAILED DESCRIPTION

Figure 1:
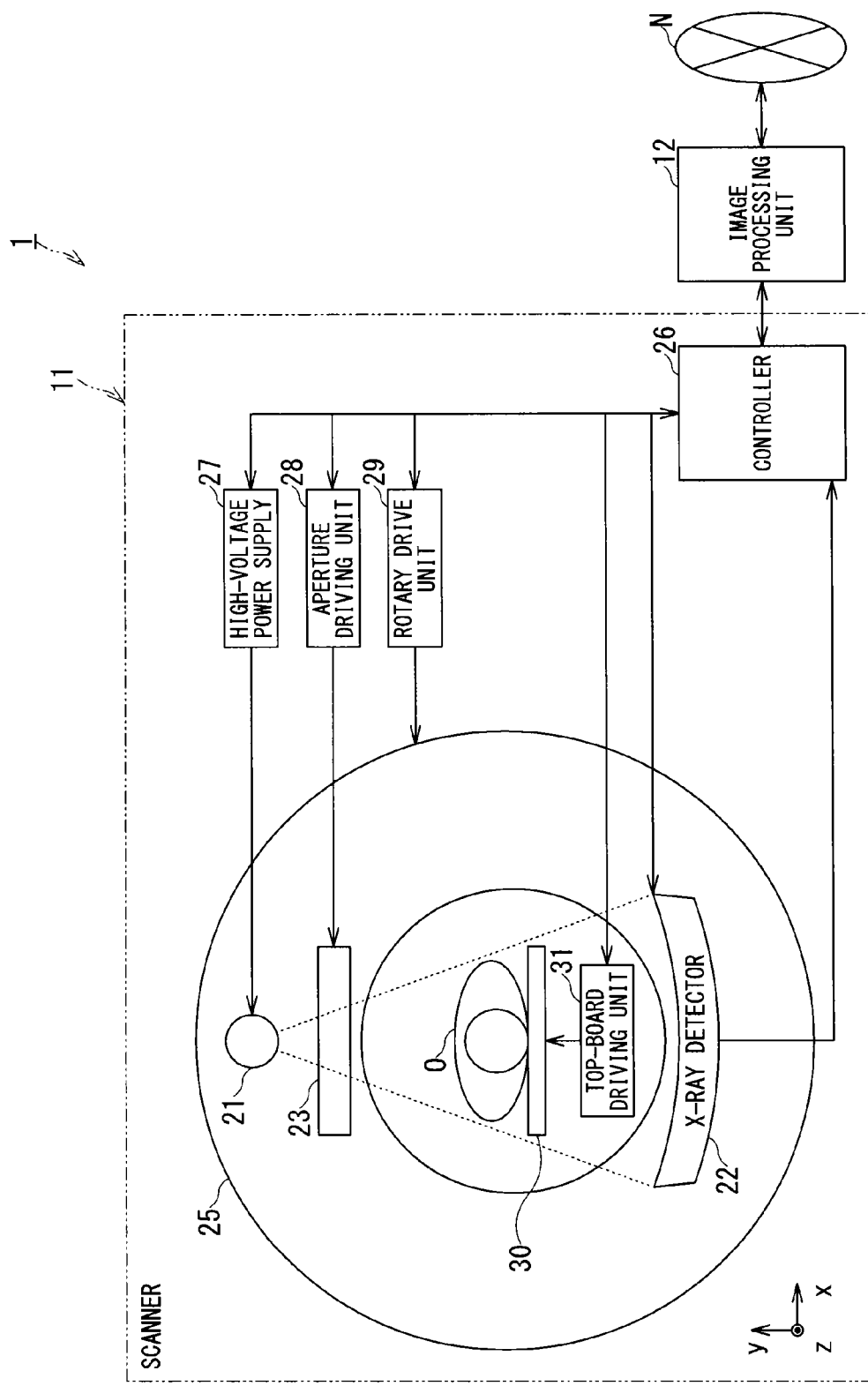
FIG. 1 is a hardware block diagram showing an X-ray CT apparatus of the present embodiment.

An X-ray detection submodule, an X-ray detection module, and an X-ray CT apparatus relating to the present embodiment will be described with reference to the appended drawings.

The present embodiments provide the X-ray detection submodule including: a substrate; a photodiode mounted on the substrate; an X-ray detection element configured to detect an X-ray and convert the X-ray into light; and a light waveguide provided between the photodiode and the X-ray detection element, wherein the light waveguide connects the X-ray detection element with the photodiode such that the substrate is inclinedly disposed with respect to an X-ray detection surface of the X-ray detection element.

According to the present embodiment, the X-ray detection submodule is able to not only reduce the occurrence of external noise, but also facilitate the handling of signals detected by an X-ray detection element, thereby allowing to improve a space utilization efficiency and also cope with the increase in the number of X-ray detection elements.

The present embodiments provide the X-ray detection module having a plurality of X-ray detection submodules, wherein each of the plurality of X-ray detection submodules comprises: a substrate; a photodiode mounted on the substrate; an X-ray detection element configured to detect an X-ray and convert the X-ray into light; and a light waveguide provided between the photodiode and the X-ray detection element, wherein the light waveguide connects the X-ray detection element with the photodiode such that the substrate is inclinedly disposed with respect to the X-ray detection surface of the X-ray detection element.

According to the present embodiment, the X-ray detection module, as with the X-ray detection submodule, is able to not only reduce the occurrence of external noise, but also facilitate the handling of signals detected by an X-ray detection element, thereby allowing to improve the space utilization efficiency and also cope with the increase in the number of X-ray detection elements.

Moreover, the X-ray CT apparatus relating to the present embodiment includes the following four features to solve conventional problems.

Specifically, the first feature is that one X-ray detection submodule is formed by adopting a light waveguide produced by using a material having an optical characteristic, instead of using a conventional wiring substrate (for example, a rigid flexible substrate). As a result of this, it is possible to make the wiring, which is a cause of the occurrence of external noise, short in length and uniformly arranged.

The second feature is that a scintillator and a photodiode are connected by a light waveguide so that a substrate to which the photodiode is mounted is inclinedly disposed with respect to the scintillator. As a result of this, it is possible to increase the space utilization efficiency in the X-ray CT apparatus.

The third feature is that each X-ray detection submodule is directly connected to each other with a connector. As a result of this, it is possible to obviate the wiring between substrates, thereby reducing the occurrence of external noise.

The fourth feature is that the output data is transferred to a connector in a subsequent stage of the connected X-ray detection submodule with a daisy chain. As a result of this, it is possible to reduce the number of wirings on the substrate.

Having the four features described above, the X-ray CT apparatus relating to the present embodiment is able to not only simply reduce the occurrence of external noise, but also facilitate the handling of signals detected by the X-ray detection element, thereby coping with the increase in the number of X-ray detection elements.

Next, an embodiment of the X-ray CT apparatus relating to the present embodiment will be described in detail with reference to the appended drawings shown below.

The X-ray CT apparatus of the present embodiment includes various types such as a rotation/rotation (ROTATE/ROTATE) type in which an X-ray tube and an X-ray detector rotate as a single body around an object, and a stationary/rotation (STATIONARY/ROTATE) type in which a large number of detection elements are arrayed in a ring shape and only the X-ray tube rotates around the object, and the present invention can be applied to any of those types. Here, description will be made assuming the ROTATE/ROTATE type which currently occupies the mainstream.

Further, as a mechanism for converting an incident X-ray into an electric charge, an indirect conversion type in which an X-ray is converted into light with a fluorescent body such as a scintillator and the light is further converted into an electric charge with a photoelectric transducer such as a photodiode, and a direct conversion type which utilizes the generation of electron-hole pairs in a semiconductor by an X-ray and the migration thereof to an electrode, that is, a photoconductive phenomenon are in the mainstream.

In addition, in recent years, the commercialization of a so-called multi-tube type X-ray CT apparatus in which a plurality of pairs of an X-ray tube and an X-ray detector are mounted on a rotation ring is in progress, and peripheral technologies thereof are also being developed. The X-ray CT apparatus of the present embodiment can be applied to either of a conventional single-tube type X-ray CT apparatus or a multi-tube type X-ray CT apparatus. Here, description will be made assuming the single-tube type X-ray CT apparatus.

FIG. 1 is a hardware block diagram showing an X-ray CT apparatus 1 relating to the present embodiment.

The X-ray CT apparatus 1 shown in FIG. 1 is made up of a scanner 11 and an image processing unit 12. The scanner 11 of the X-ray CT apparatus 1 is generally installed in an examination room, and is configured to generate X-ray transmission data relating to an exposure area of an object (a human body) O. On the other hand, the image processing unit 12 is generally installed in a control room next to the examination room, and is configured to produce projection data based on the transmission data, thereby generating and displaying a reconstructed image.

The scanner 11 of the X-ray CT apparatus 1 includes an X-ray tube 21 as an X-ray source, an X-ray detector 22, an aperture 23, a rotating portion 25, a controller 26, a high-voltage power supply 27, an aperture driving unit 28, a rotary drive unit 29, a top board 30, and a top-board driving unit (a bed unit) 31.

The X-ray tube 21 is adapted to radiate an X-ray toward the X-ray detector 22 depending on a tube voltage supplied from the high-voltage power supply 27. A fan beam X-ray and a cone beam X-ray are formed by the X-ray radiated from the X-ray tube 21.

The X-ray detector 22 is a two-dimensionally arrayed X-ray detector (also referred for as a multi-slice type detector) which has X-ray detection elements in a plurality of (M) channels in a direction perpendicular to the longitudinal direction of the top board (a channel direction), which is the body-axis direction of the object O, and a plurality of (N) rows in the longitudinal direction of the top board (a row direction). The X-ray detector 22 is radiated from the X-ray tube 21, and is adapted to detect the X-ray that has transmitted through the object O.

Moreover, the X-ray detector 22 is made up of a plurality of X-ray detection modules. Furthermore, the X-ray detection modules are each made up of a plurality of X-ray detection submodules. Further, each of the plurality of X-ray detection submodules is mounted with a scintillator (an X-ray detection element) for detecting an X-ray, a photodiode for converting the detected X-ray into an electric signal, and a conversion element for converting the electric signal outputted by the photodiode into a digital signal.

The conversion element is adapted to convert and amplify an electric signal of the transmission data detected by each X-ray detection element of the X-ray detector 22 into a voltage signal, and further convert it into a digital signal.

The X-ray detector 22 is adapted to output the converted digital data (raw data) to the image processing unit 12 via the controller 26. It is noted that details of the X-ray detector 22 will be described later.

The aperture 23 adjusts a radiation range in the row direction of an X-ray radiated from the X-ray tube 21 by being driven by the aperture driving unit 28. That is, the aperture 23 is adapted to change the X-ray radiation range in the row direction by the aperture driving unit 28 adjusting the opening of the aperture 23.

The rotating portion 25 is accommodated in a stand (not shown) of the scanner 11, and is adapted to hold the X-ray tube 21, the X-ray detector 22, and the aperture 23 as a single body. The rotating portion 25 is configured such that the X-ray tube 21, the X-ray detector 22 and the aperture 23 can be rotated as a single body around the object O with the X-ray tube 21 and the X-ray detector 22 being disposed facing each other.

The controller 26 is made up of a CPU (Central Processing Unit) and a memory. The controller 26 is adapted to control the X-ray detector 22, the high-voltage power supply 27, the aperture driving unit 28, the rotary drive unit 29, the top-board driving unit 31 and the like based on a control signal inputted from the image processing unit 12 to make scanning motion.

The high-voltage power supply 27 is adapted to supply electric power required for the radiation of X-ray to the X-ray tube 21 through the control by the controller 26.

The aperture driving unit 28 is adapted to perform the driving of the aperture 23 for adjusting the radiation range of X-ray in the row direction through the control by the controller 26.

The rotary drive unit 29 rotates the rotating portion 25 such that the rotating portion 25 rotates around the opening portion while maintaining the positional relationship therebetween through the control by the controller 26.

The object O can be placed on the top board 30.

The top-board driving unit 31 drives the top board 30 so as to move it along a z-axis direction (a body-axis direction) through the control by the controller 26. The rotating portion 25 has an opening in its central portion, and the object O placed on the top board 30 is inserted into the opening portion along the z direction.

The image processing unit 12 of the X-ray CT apparatus 1 is adapted to perform correction processing (preprocessing) such as logarithmic conversion and sensitivity correction on the raw data inputted from the X-ray detector 22 of the scanner 11 to generate projection data.

Moreover, the image processing unit 12 performs the process of removing scattered rays on the preprocessed projection data. The image processing unit 12, which is adapted to perform the removal of scattered rays base on the value of the projection data within the X-ray radiation range, performs scattered ray correction by subtracting projection data, which is to be subjected to scattered ray correction, or a scattered ray, which is estimated from the magnitude of the value of projection data adjacent to the aforementioned one, from the target projection data. The image processing unit 12 is adapted to generate a reconstructed image based on the corrected projection data.

Further, the image processing unit 12 is constructed on the basis of a computer, and can intercommunicate with a network N such as a backbone LAN (Local Area Network) of a hospital. Moreover, the image processing unit 12 is made up of, though not shown, basic hardware such as a CPU, a memory, an HDD (Hard Disc Drive), an input device and a display device, etc.

Next, the configurations of the X-ray tube 21 and the X-ray detector 22 relating to the present embodiment will be described.

Figure 2:
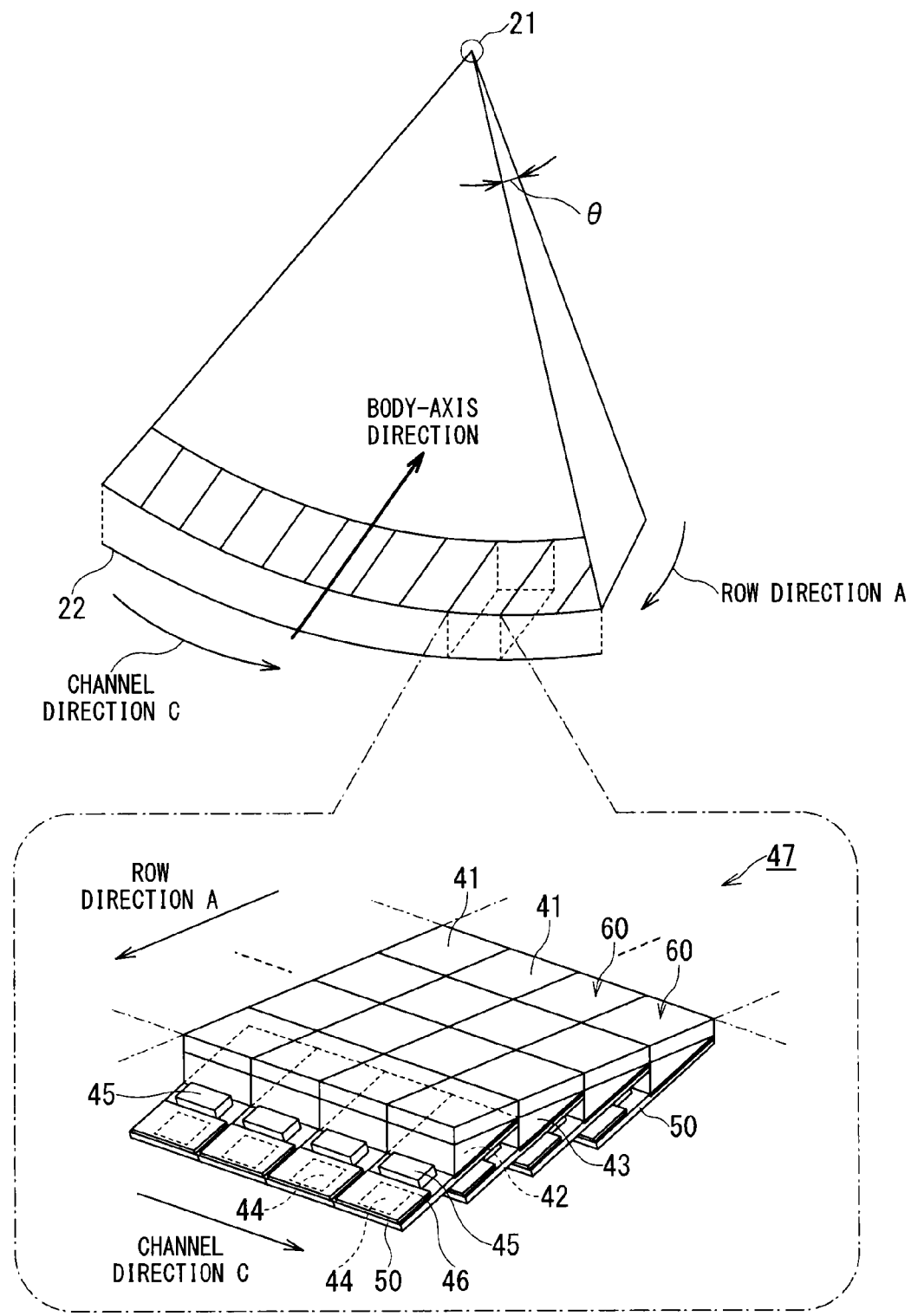
FIG. 2 is an explanatory diagram showing the configurations of an X-ray tube and an X-ray detector relating to the present embodiment.

FIG. 2 is an explanatory diagram showing the configurations of the X-ray tube 21 and the X-ray detector 22 relating to the present embodiment.

As shown in FIG. 2, the X-ray tube 21 and the X-ray detector 22 are disposed opposing to each other at a position where they can rotate in a channel direction C which is in a plane approximately perpendicular to the body-axis direction of the object O (or a row direction A). Moreover, the X-ray detector 22 is constituted by a plurality of X-ray detection modules 47.

In the X-ray detection module 47 shown in FIG. 2, as an example, one unit of X-ray detection module is made up of 16 X-ray detection submodules 60, which are arranged in 4 channels by 4 rows. That is, the X-ray detection module 47 is configured such that 16 substrates 50 arranged in 4 channels by 4 rows are each connected to a scintillator 41 of each X-ray detection submodule 60 by a light waveguide 43, thereby forming one unit of X-ray detection module.

Here, one unit is not limited by the numbers of channels and rows, and can make up an X-ray detection module in which a desired one unit is constituted by, for example, 1 channel by 4 rows, or 2 channels by 2 rows.

Moreover, as shown in FIG. 2, the X-ray detection module 47 is configured such that 4 rows of X-ray detection submodules 60 are aligned along the row direction A, and each substrate 50 is inclinedly disposed (at a predetermined angle) with respect to the scintillator 41 of each X-ray detection submodule 60.

Here, the inclined disposition of the substrate 50 means that each substrate 50 is respectively disposed at a position where the X-ray detection surface of the scintillator 41 and the substrate 50 form a predetermined angle so as to be non-parallel with each other.

Such configuration allows the X-ray CT apparatus 1 relating to the present embodiment to increase the space utilization efficiency in the X-ray CT apparatus 1.

Further, each substrate 50 of the X-ray detection submodule 60 includes an ADC 44, a connector 45, and a shield lead (shield membrane) 46. Each substrate 50 is configured such that substrates which are adjacent to each other in the row direction A are connected by a connector 45. Moreover, at an end row (the row of the X-ray detection submodules 60 located at the endmost in the row direction), substrates 50 which are adjacent to each other in the channel direction C are connected by a connector.

Thus, as a result of that each substrate 50 is connected in the row direction A by the connector 45, the X-ray detection module 47 can output a signal by a daisy chain, and even at the end row, adjacent substrates 50 can output a signal to each other by a daisy chain.

Therefore, the X-ray detection submodule 60 relating to the present embodiment can easily realize the data output per a unit of the X-ray detection module 47, thereby reducing the number of wirings among each substrate 50, and reducing the occurrence of external noise. Further, since an X-ray detection module 47 constituted by various numbers of channels and rows can be constructed, it is possible to realize a tiling arrangement with a high degree of freedom, thereby attaining a desired X-ray detector 22 with ease.

Moreover, although the substrate 50 constituting each X-ray detection submodule 60 is inclinedly disposed with respect to the scintillator 41 of each X-ray detection submodule 60, the gradient of this inclination will not be limited specifically. That is, due to the gradient of the inclination, for example, even if the upper surface of the photodiode 42 placed on the substrate 50 is inclined such that the head part of the object O is lower, or the leg part is lower, it is possible to realize the X-ray detector 22 as well.

Further, although the gradient of the inclination at which the substrate 50 is disposed is inclined in the row direction in FIG. 2, it may be inclined in the channel direction C.

It is noted that since a large number (for example, 1000) of detectors are disposed in the channel direction C, the X-ray CT apparatus 1 is preferably disposed to be inclined in the illustrated row direction A when taking account of the assembly and maintenance of the X-ray CT apparatus 1.

Next, the configuration of the X-ray detection submodules 60 constituting the X-ray detection module 47 will be described in detail.

Figure 3A:
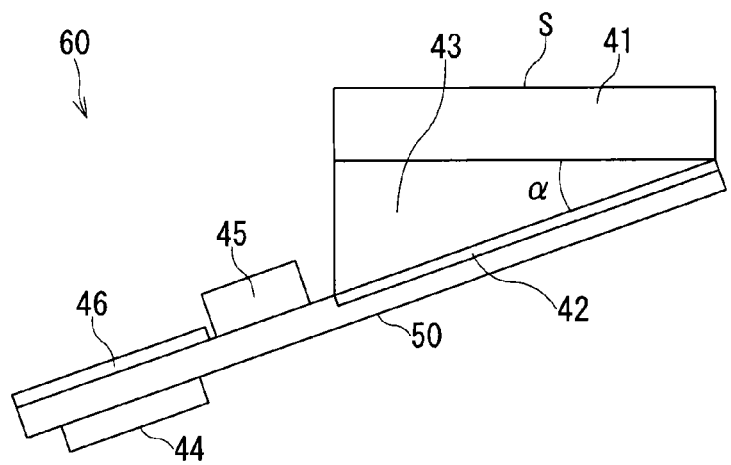
FIG. 3A-3C are explanatory diagrams illustrating the configuration of an X-ray detection submodule relating to the present embodiment.
Figure 3B:
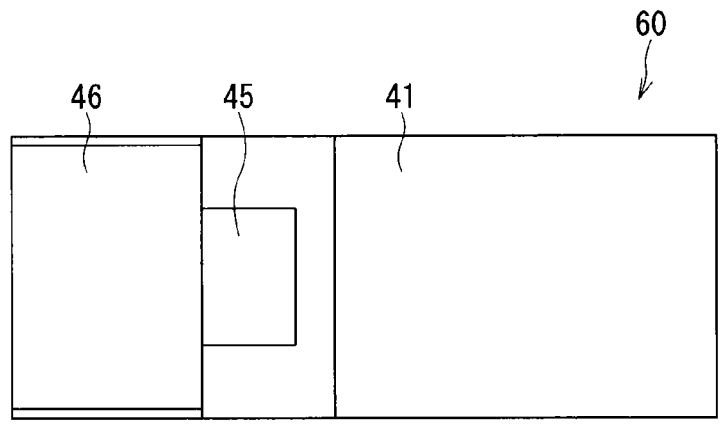
Figure 3C:
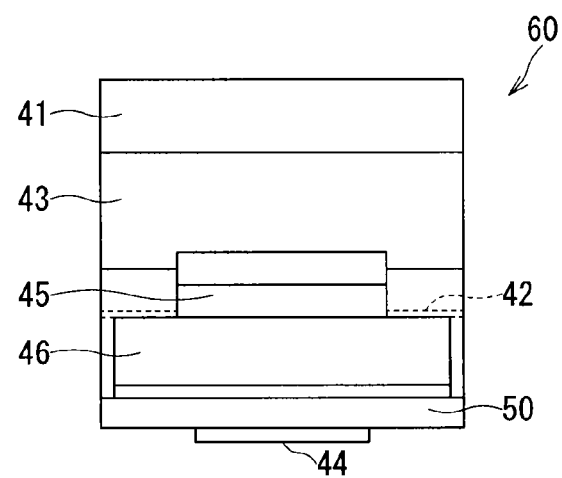

FIG. 3A-3C are explanatory diagrams illustrating the configuration of an X-ray detection submodule 60 relating to the present embodiment.

FIG. 3A shows a cross sectional view of the X-ray detection submodule 60 taken along the body axis and seen in the channel direction C. The substrate 50 is inclinedly disposed with respect to the scintillator 41 by means of a light waveguide 43 so as to form a predetermined angle α therebetween.

The substrate 50 includes a photodiode 42, an ADC 44, a connector 45, and a shield lead 46.

The photodiode 42 acquires light from the scintillator 41 via the light waveguide 43, and converts it into an electric signal. Then, the photodiode 42 sends the converted electric signal out to the ADC 44.

The light waveguide 43 is a transmission path for inclinedly disposing the substrate 50 with respect to the scintillator 41 (more specifically, with respect to an X-ray detection surface S of the scintillator 41). This light waveguide 43 is a transmission path which is produced by using a material having an optical property. To be specific, it is a transmission path that guides light having high straightness by utilizing the difference in the refraction index of light. Further, the light waveguide 43 is a concept encompassing optical fibers, and its light path has the same structure as that of the optical fiber. It is noted that although the light waveguide 43 generally has a sheet-shaped or plate-shaped structure, it has a wedge shape as shown in the figure, which is a characteristic feature of the present embodiment.

The ADC 44 performs conversion processing from an analog single to a digital signal (A/D conversion processing) upon acquisition of a converted electric signal. Then, the converted digital signal is sent out to the next substrate 50 which is connected thereto in the row direction A (FIG. 2) via the connector 45.

Here, although the connector 45 is provided between the scintillator 41 and the shield lead 46 with respect to the surface of the page (FIG. 3A), the position of the connector 45 will not be limited thereto. For example, the connector 45 may be provided on the left side of the shield lead 46 with respect to the surface of the page (FIG. 3A). In this case, since the photodiode 42 and the ADC 44 can be placed closer to each other, it is possible to suppress the occurrence of external noise due to a large wiring length.

The shield lead 46 is provided for shielding the ADC 44, and to prevent the ADC 44 from being destroyed by an X-ray which unintentionally transmits the substrate 50, a shield lead 46, which has a size larger than that of the ADC 44, is provided on the side of the substrate 50 opposite to the surface on which the ADC 44 is placed, and at a position opposing to the ADC 44.

To be specific, since the photodiode 42 is placed (mounted) on the substrate 50, and the ADC 44 is placed on the surface opposite to the surface where the photodiode 42 is placed, the shield lead 46 is provided at a position where it opposes the ADC 44 with the substrate 50 being interposed therebetween, in such a way to cover the ADC 44.

FIG. 3B is an explanatory view when the X-ray detection submodule 60 is viewed in the direction to the X-ray detector 22 (FIG. 2) from the position of the X-ray tube 21 (FIG. 2), that is, viewed from right above. When the X-ray detection submodule 60 is viewed from right above, the substrate 50 is provided with the scintillator 41, the connector 45 and the shied lead 46.

FIG. 3C is a sectional view of the X-ray detection submodule 60 viewed from the left side to the right side with respect to FIG. 3A. The X-ray detection submodule 60 is provided with the scintillator 41, the light waveguide 43, the photodiode 42, the connector 45, and the shield lead 46 on the substrate 50. Further, the ADC 44 is provided on the substrate 50 at a position opposite to (opposing to) the position where the shield lead 46 is provided.

In the above described FIG. 3A to 3C, although the positional relationship between the scintillator 41 and the substrate 50 in the X-ray detection submodule 60 is mainly described, the present embodiment will not be limited thereto. To be specific, a configuration in which the scintillator 41 is removed from the X-ray detection submodule 60 may be formed as a light detection submodule for detecting light.

Next, the operation of the X-ray CT apparatus 1 relating to the present embodiment will be described by using a flowchart.

(Image Data Generating Process)

Figure 4:
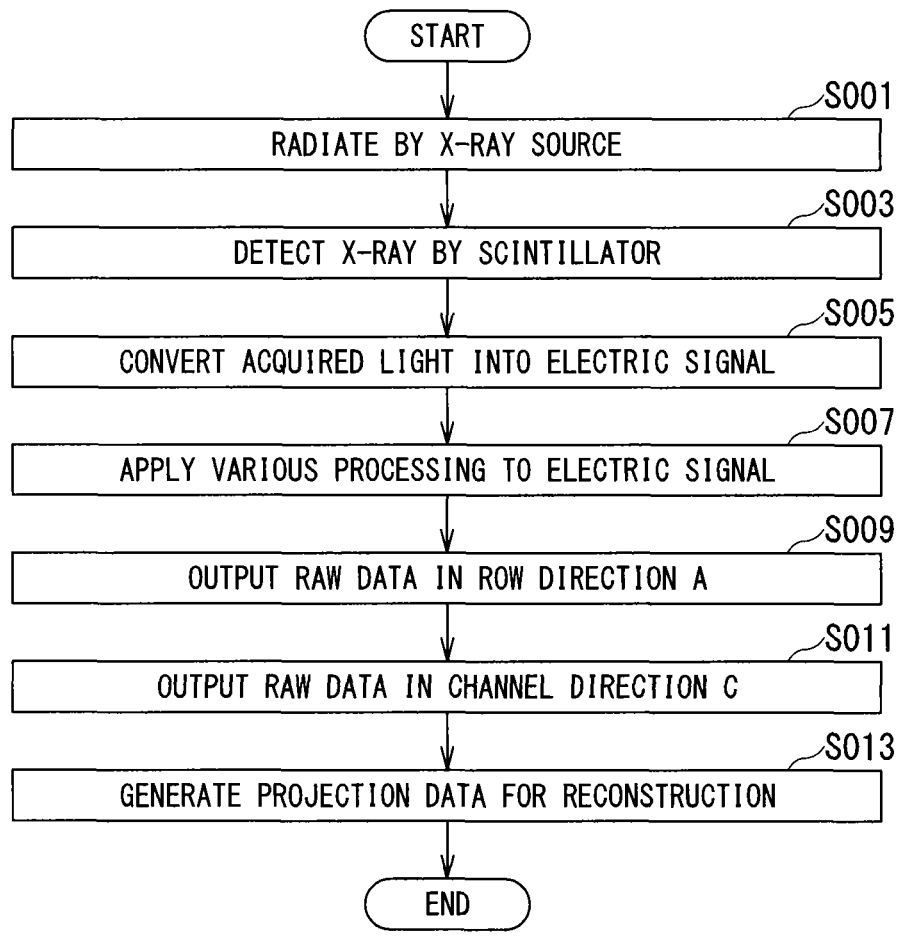
FIG. 4 is a flowchart showing an image data generating process for generating image data of a desired slice image by radiating an X-ray with an X-ray CT apparatus relating to the present embodiment.

FIG. 4 is a flowchart showing an image data generating process for generating image data of a desired slice image by radiating an X-ray with the X-ray CT apparatus 1 relating to the present embodiment.

As shown in FIG. 4, first, the X-ray tube 21 and the X-ray detector 22 of the X-ray CT apparatus 1 spirally rotate around the object O, and a tube current by a predetermined tube voltage from a high-voltage power supply 27 is supplied to the X-ray tube 21 by a control signal from the controller 26. As a result of this, an X-ray having desired energy is radiated to the object O from each rotational position of the X-ray tube 21 (step S001).

The X-ray that has transmitted the object O is detected by each scintillator 41 of the X-ray detection module 47 constituting the X-ray detector 22. That is, the scintillator 41 converts an X-ray incident to the X-ray detector 22 into light, and supplies it to the photodiode 42 (step S003).

The photodiode 42 converts the light acquired from the scintillator 41 via the light waveguide 43 into an electric signal (step S005).

The ADC 44 applies processing such as amplification, A/D conversion, and the like to the X-ray detection data that has been converted into an electric signal (step S007). As a result of this, the ADC 44 generates a digital signal (this is also referred to as raw data) corresponding to the X-ray detection data detected by the scintillator 41.

The X-ray detection module 47 outputs the raw data generated at the ADC 44 in the row direction A via the connector 45 (step S009).

Next, the method in which the X-ray detection module 47 outputs the raw data in the row direction A will be described by using the drawings.

Figure 5:
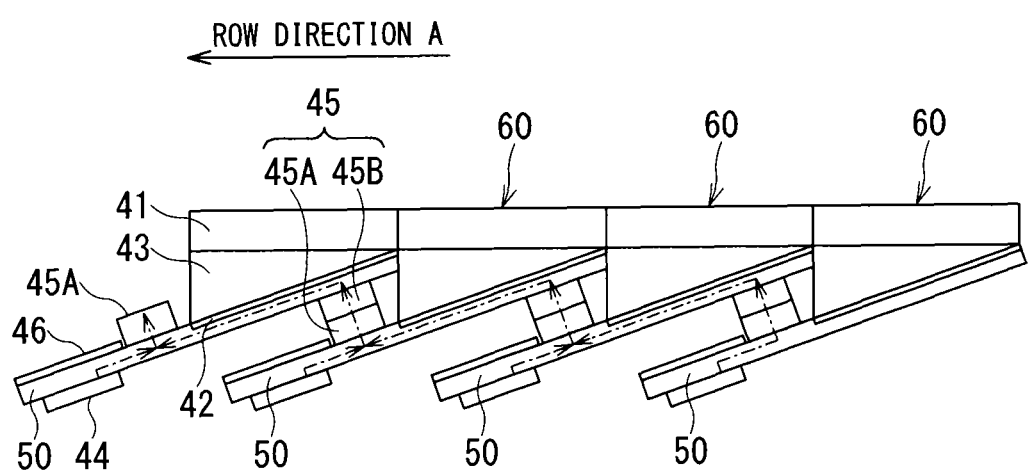
FIG. 5 is an explanatory diagram illustrating a method for outputting raw data in a row direction (from the right side to the left side with respect to the surface of the page of FIG. 5) by the configuration of four X-ray detection submodules that constitute a part of an X-ray detection module relating to the present embodiment.

FIG. 5 is an explanatory diagram to illustrate a method of outputting raw data in the row direction A (the direction from the right side to the left side with respect to the surface of the page of FIG. 5) by the configuration of four X-ray detection submodules 60 that constitute a part of the X-ray detection module 47 relating to the present embodiment. It is noted that the like components are given the like reference symbols, thereby appropriately omitting the description thereof.

In FIG. 5, substrates 50 are disposed so as to overlap with each other in each substrate 50 of the four X-ray detection submodules 60 which are adjacent to each other in the row direction A. Moreover, each substrate 50 is disposed respectively at a position where the X-ray detection surface of the scintillator 41 and the substrate 50 form a predetermined angle so as to be non-parallel with each other.

Further, as shown in FIG. 5, the connector 45 provided on the substrate 50 is made up of a connector 45A provided on the substrate 50 on the side of the X-ray tube 21 (on the side facing the scintillator 41), and a connector 45B provided on the substrate 50 on the opposite side to the X-ray tube 21 (on the opposite side to the scintillator 41).

The X-ray detection module 47 successively outputs raw data in the row direction A by a daisy chain by connecting the substrates 50 of the X-ray detection submodules 60, which are adjacent to each other in the row direction A, with the connector 45A and the connector 45B.

Moreover, in the present embodiment, the raw data is outputted from the ADC 44 of the substrate 50 that is located left-most with respect to the surface of the page (FIG. 5) via the connector 45A such that the raw data that has been converted into a digital signal at the ADC 44 is successively outputted. After the raw data is outputted, the raw data of the ADC 44 of the substrate 50 located next on the right with respect to the surface of the page (FIG. 5) is outputted in succession.

Since in this way, first, the raw data of the ADC 44 of the substrate 50 located leftmost with respect to the surface of the page (FIG. 5) is outputted, and next, the raw data of the ADC 44 of the substrate 50 located next on the right is outputted by the daisy chain, the X-ray detection module 47 can successively output the raw data at the ADC 44 of each substrate 50 in the row direction A.

Then, when the processing of outputting the raw data in the row direction A in step S009 shown in FIG. 4 is finished, the X-ray detection module 47 outputs the raw data in the channel direction C at an end row (step S011 of FIG. 4).

Next, the method in which the X-ray detection module 47 outputs raw data in the channel direction C will be described by using the drawings.

Figure 6:
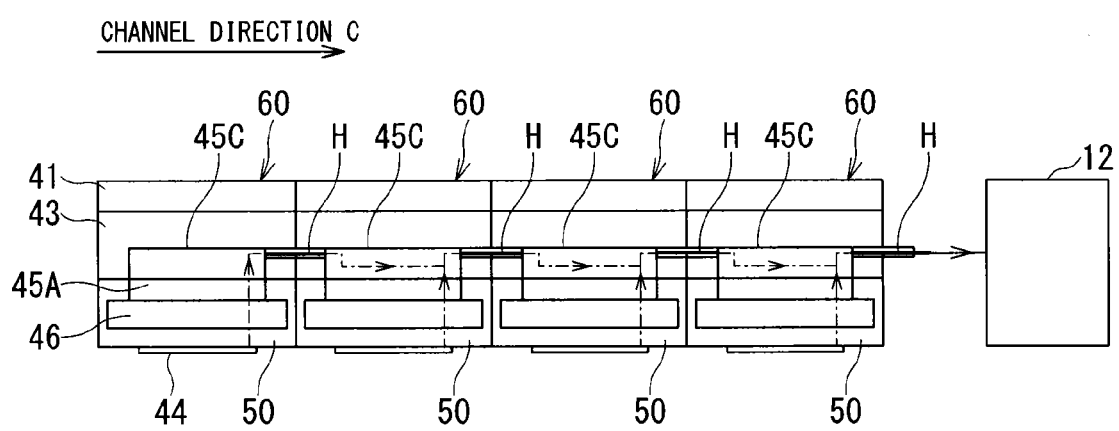
FIG. 6 is an explanatory diagram illustrating a method for outputting raw data in a channel direction (from the left side to the right side with respect to the surface of the page of FIG. 6) by the configuration of four X-ray detection submodules that constitute a part of the X-ray detection module relating to the present embodiment.

FIG. 6 is an explanatory diagram illustrating a method for outputting raw data in the channel direction C (from the left side to the right side with respect to the surface of the page of FIG. 6) by the configuration of four X-ray detection submodules that constitute a part of the X-ray detection module relating to the present embodiment. It is noted that the like components are given the like reference symbols, thereby appropriately omitting the description thereof.

FIG. 6 shows that four X-ray detection submodules 60 are disposed adjacent to each other in the channel direction C at the end row. As shown in FIG. 6, the connector 45C provided on the substrate 50 of each X-ray detection submodule 60 is connected by a wiring H at the end row. For this reason, it is possible to output raw data in the channel direction C by a daisy chain at the end row of the X-ray detection module 47.

Moreover, the order of outputting the raw data is arranged such that the raw data is outputted in order from the X-ray detection submodule 60 which is located on the right-most side with respect to the surface of the page (FIG. 6). That is, in FIG. 6, after the raw data is successively outputted in the row direction A from the connector 45C of the substrate 50 of the X-ray detection submodule 60 which is located on the right-most side with respect to the surface of the page (FIG. 6), next, from the connector 45C of the substrate 50 of the X-ray detection submodule 60 which is adjacent on the left side to the aforementioned X-ray detection submodule 60, the raw data in the row direction A is successively outputted via the wiring H.

It is noted that the above described connector 45C is a connector having a shape for connecting with the connector 45A, and is an equivalent with the connector 45B. By mounting this connector 45C to the connector 45A at the end row (the connector 45A on the left-most side in FIG. 5) shown in FIG. 5, it is possible to realize a daisy chain at the end row shown in FIG. 6.

Then, when the processing of outputting the raw data in the channel direction C in step S011 shown in FIG. 4 is finished, the X-ray detector 22 outputs the raw data to the image processing unit 12 via the controller 26.

Upon acquiring the raw data generated by the X-ray detection module 47, the image processing unit 12 performs correction processing (preprocessing) such as logarithmic conversion and sensitivity correction, on the inputted raw data to generate projection data. Moreover, the image processing unit 12 performs the processing such as removal of scattered rays on the preprocessed projection data to generate a reconstructed image based on the corrected projection data (step S013).

As described so far, since the X-ray CT apparatus 1 relating to the present embodiment is configured such that the substrate 50 to which the photodiode 42 is mounted is inclinedly disposed with respect to the scintillator 41 in the X-ray detection submodule 60, it is possible to place the ADC 44 and the photodiode 42 on the substrate 50.

Further, since the X-ray detection module 47 can realize an X-ray detection module made up of desired M channels by N rows by a plurality of X-ray detection submodules 60, it is possible to decrease the length of the wiring from the scintillator 41 to the ADC 44, and uniformly arrange the wiring.

As a result of this, the X-ray CT apparatus 1 relating to the present embodiment can suppress the occurrence of external noise caused by a large wiring length, and increase the certainty of the signal.

Further, it is possible to easily construct one unit of the X-ray detection module 47 which is constituted by X-ray detection submodules 60 arranged in desired M channels by N rows, and the user can construct a desired X-ray detector 22 by disposing the X-ray detection modules 47 in a tiling arrangement.

Further, in the flowchart shown in FIG. 4, after the raw data outputted from the ADC 44 of the X-ray detection submodule 60 is outputted in the row direction A in step S009, the raw data is outputted in the channel direction C in step S011, but the present invention is not limited to this embodiment.

For example, when making up an X-ray CT apparatus 1 based on a simultaneous collection system, the method of outputting the raw data in the row direction A in step S009 and the method of outputting the raw data in the channel direction C in step S011 may be carried out alternatively with each other.

Although a couple of embodiments of the invention are explained, these embodiments are exemplary only and it is not intended that the scope of the invention is limited by the embodiments. These embodiments can be put into practice in other various forms, and can be variously omitted, replaced or changed within the scope of the invention. The embodiments and their modifications are included in the scope and the coverage of the invention, and similarly in the equivalents to the claimed invention.

Further, in the embodiments of the present invention, although an example of processing in which each step of the flowchart is successively is carried out in time series according to the stated order has been shown, processing in which each step is carried out not necessarily in time series, but in parallel or on an individual basis may be included.

What is claimed is:

1. An X-ray detection submodule comprising:
a substrate;
a photodiode mounted on the substrate;
an X-ray detection element configured to detect an X-ray and convert the X-ray into light;
a light waveguide provided between the photodiode and the X-ray detection element; and
a connector connected to a connector of an adjacent X-ray detection submodule so as to support the adjacent X-ray detection submodule, wherein
the light waveguide connects the X-ray detection element with the photodiode such that the substrate is inclinedly disposed with respect to an X-ray detection surface of the X-ray detection element.

2. The X-ray detection submodule according to claim 1, wherein
when the substrate is inclinedly disposed, the substrate is disposed at a position where the X-ray detection surface of the X-ray detection element and the substrate form a predetermined angle so as to be non-parallel with each other.

3. An X-ray detection submodule comprising:
a substrate;
a photodiode mounted on the substrate;
an X-ray detection element configured to detect an X-ray and convert the X-ray into light;
a light waveguide connected the X-ray detection element with the photodiode such that the substrate is inclinedly disposed with respect to an X-ray detection surface of the X-ray detection element; and
a conversion element configured to convert an electric signal outputted by the photodiode into a digital signal, wherein
the conversion element is provided with a shield membrane for shielding the X-ray, the shield membrane being disposed on a surface of the substrate on a same side as a surface to which the photodiode is mounted, and at a position opposing to the conversion element.

4. An X-ray detection module having a plurality of X-ray detection submodules, wherein
each of the plurality of X-ray detection submodules comprises:
a substrate;
a photodiode mounted on the substrate;
an X-ray detection element configured to detect an X-ray and convert the X-ray into light; and
a light waveguide provided between the photodiode and the X-ray detection element; and
a connector connected to a connector of an adjacent X-ray detection submodule so as to support the adjacent X-ray detection submodules with each other, wherein
the light waveguide connects the X-ray detection element with the photodiode such that the substrate is inclinedly disposed with respect to the X-ray detection surface of the X-ray detection element.

5. An X-ray detection module having a plurality of X-ray detection submodules, wherein
each of the plurality of X-ray detection submodules comprises:
a substrate;
a photodiode mounted on the substrate;
an X-ray detection element configured to detect an X-ray and convert the X-ray into light; and
a light waveguide connected the X-ray detection element with the photodiode such that the substrate is inclinedly disposed with respect to the X-ray detection surface of the X-ray detection element, wherein
when the substrate is inclinedly disposed, the substrate is disposed at a position where the X-ray detection surface of the X-ray detection element and the substrate form a predetermined angle so as to be non-parallel with each other such that in the X-ray detection submodules which are adjacent to each other in a row direction showing a body-axis direction of an object, the substrates of the X-ray detection submodules overlap with each other.

6. The X-ray detection module according to claim 4, wherein
each connector of the plurality of X-ray detection submodules is connected to a connector of the adjacent X-ray detection submodule so as to transfer data by a daisy chain in a row direction showing a body-axis direction of an object.

7. The X-ray detection module according to claim 4, wherein
each connector of the plurality of X-ray detection submodules is connected to a connector of the adjacent X-ray detection submodule such that the X-ray detection submodules, which are located at a terminal end of a row direction showing a body-axis direction of an object, transfer data to each other by a daisy chain in a channel direction perpendicular to the row direction.

8. An X-ray CT apparatus, comprising:
an X-ray source configured to radiate an X-ray to an object;
a plurality of X-ray detection submodules including:
a substrate;
a photodiode mounted on the substrate;
an X-ray detection element configured to detect the X-ray and convert the X-ray into light;
a light waveguide disposed between the photodiode and the X-ray detection element;
a connector connected to a connector of an adjacent X-ray detection submodule so as to support the adjacent X-ray detection submodule; and
a conversion element configured to convert an electric signal outputted by the photodiode into a digital signal; and
an image processing section configured to reconstruct a tomographic image of the object from the converted digital signal, wherein
the light waveguide of the X-ray detection submodule connects the X-ray detection element with the photodiode such that the substrate is inclinedly disposed with respect to an X-ray detection surface of the X-ray detection element.

* * * * *